United States Patent [19]

Murakami

[11] Patent Number: Plant 7,327

[45] Date of Patent: Sep. 18, 1990

[54] APPLE TREE NAMED 'BENIFUJI'

[75] Inventor: Tsuneo Murakami, Aomori, Japan

[73] Assignee: Hideki Otani, Reedley, Calif.

[21] Appl. No.: 274,501

[22] Filed: Nov. 21, 1988

[51] Int. Cl.[5] ..... A01H 5/00

[52] U.S. Cl. ..... Plt./34

[58] Field of Search ..... Plt./34

[56] References Cited

PUBLICATIONS

Fogle H. W., et al., "Apple", *North American and European Fruit and Tree Nut Germplasm Resources Inventory,* U.S.D.A. Misc. Pub. No. 1406, 1981 (portions) of, pp. 60,61.

*Primary Examiner*—James R. Feyrer

*Attorney, Agent, or Firm*—Staas & Halsey

[57] ABSTRACT

A new variety of apple tree is disclosed characterized by fruit which has less skin russet than Kitanosachi variety but a color, eating quality and maturing time resembling Fuji.

6 Drawing Sheets

BACKGROUND OF THE INVENTION

The present invention relates to a new and distinct variety of apple tree given the denomination Benifuji.

SUMMARY OF THE INVENTION

The primary, distinctive features of this new variety over existing varieties are fruit which has less skin russet than Kitanosachi variety, but a color, eating quality and maturing time resembling Fuji.

BRIEF DESCRIPTION OF THE VARIOUS FIGURES OF THE DRAWINGS

DESCRIPTION OF THE PREFERRED EMBODIMENTS

Figure 1:
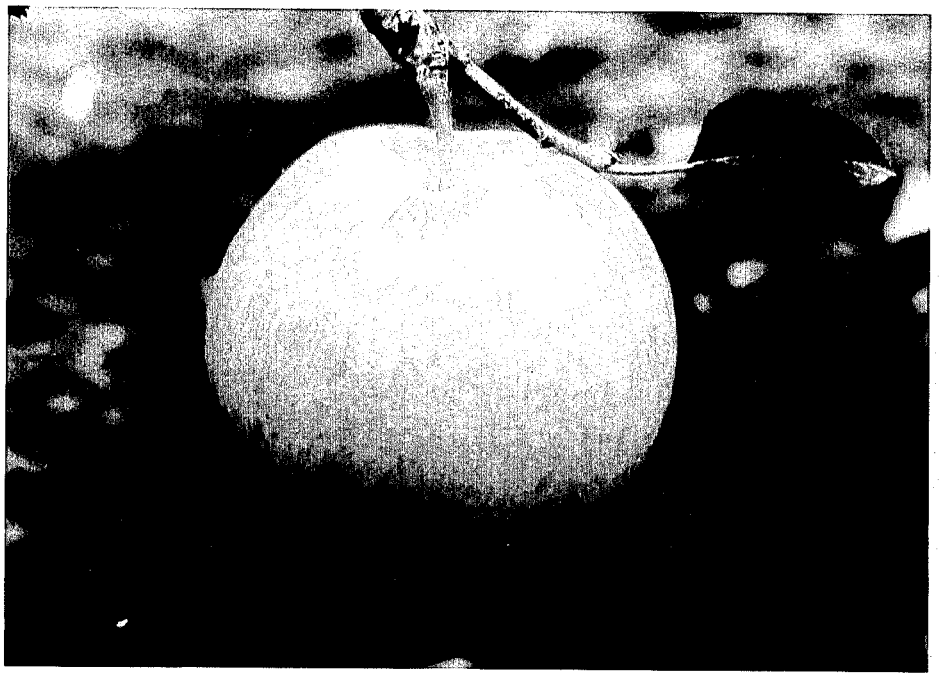
FIG. 1 is a photograph of the fruit of the new apple tree variety.
Figure 2:
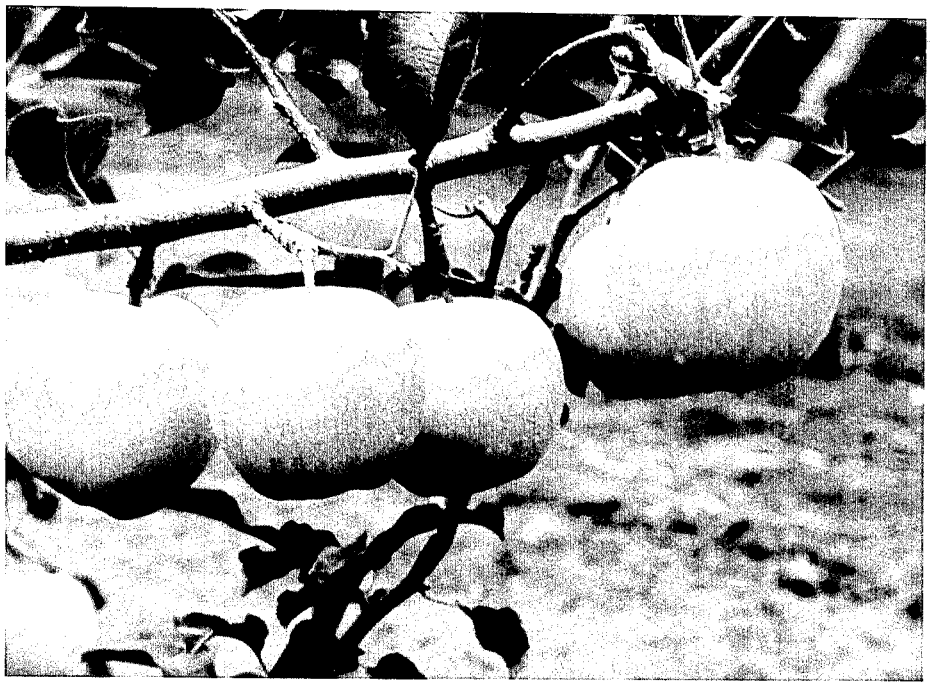
FIG. 2 is a photograph of the fruit of the new apple tree variety.
Figure 3:
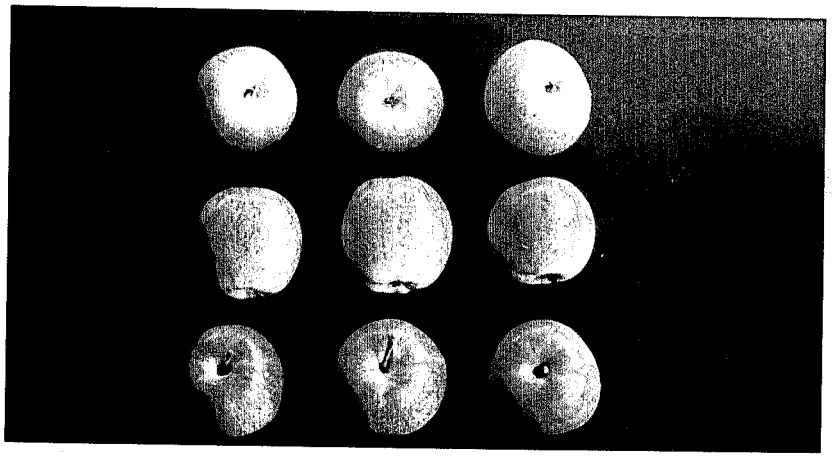
FIG. 3 is a photograph of the fruit of the new apple tree variety.
Figure 4:
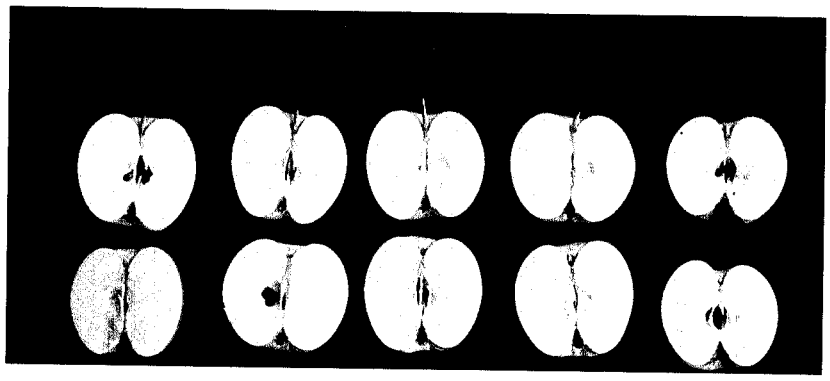
FIG. 4 is a photograph of the fruit of the new apple tree variety in longitudinal section.
Figure 5:
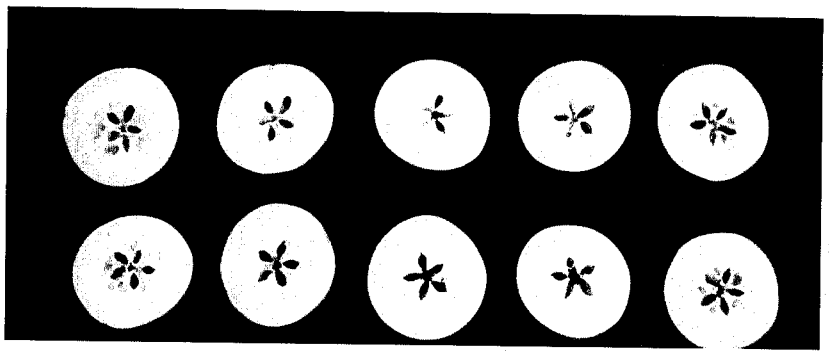
FIG. 5 is a photograph of the fruit of the new apple tree variety in cross section.
Figure 6:
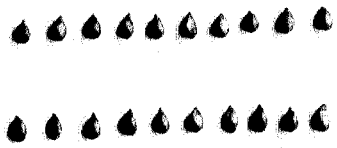
FIG. 6 is a photograph of the seeds of the new apple tree variety.
Figure 7:
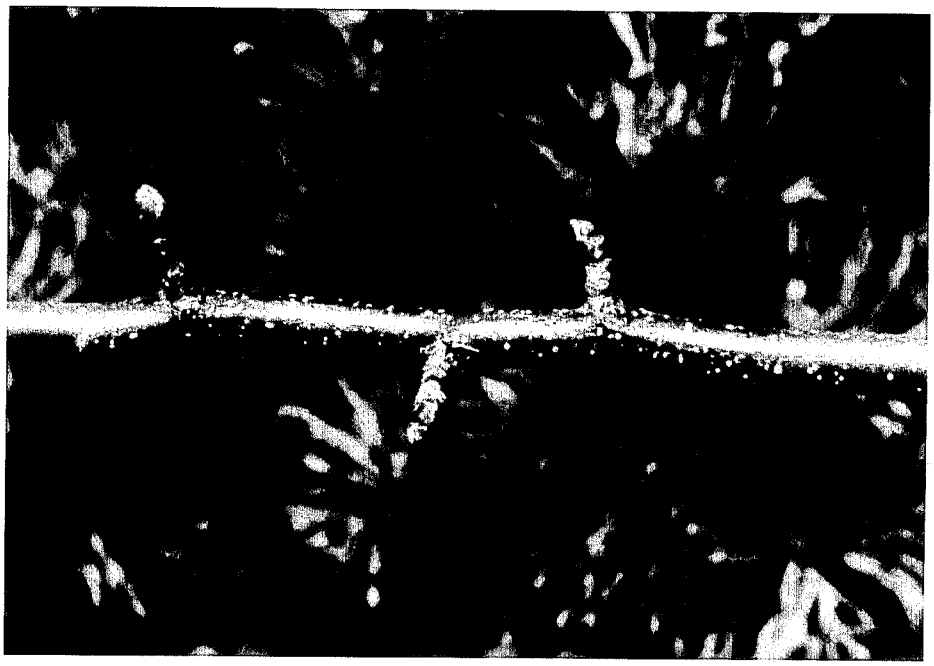
FIG. 7 is a photograph of a shoot of the new apple tree variety.
Figure 8:
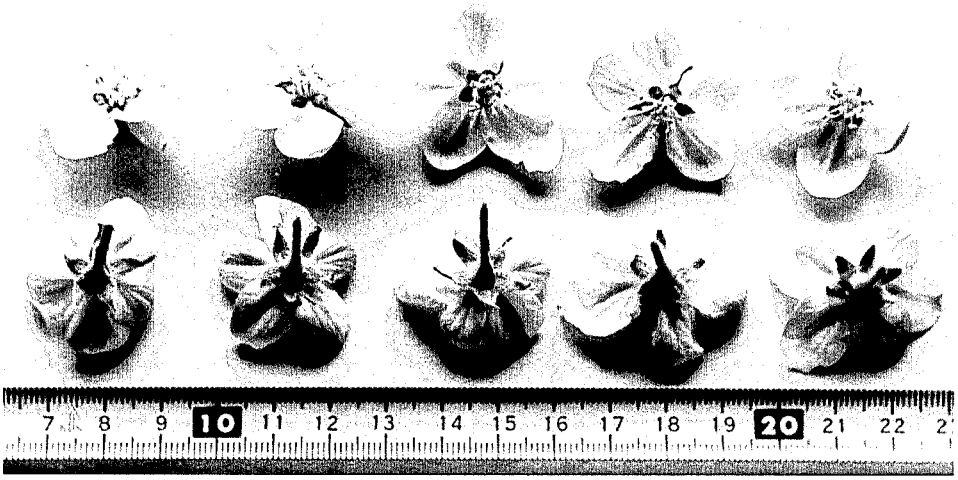
FIG. 8 is a photograph of flowers of the new apple tree variety.
Figure 9:
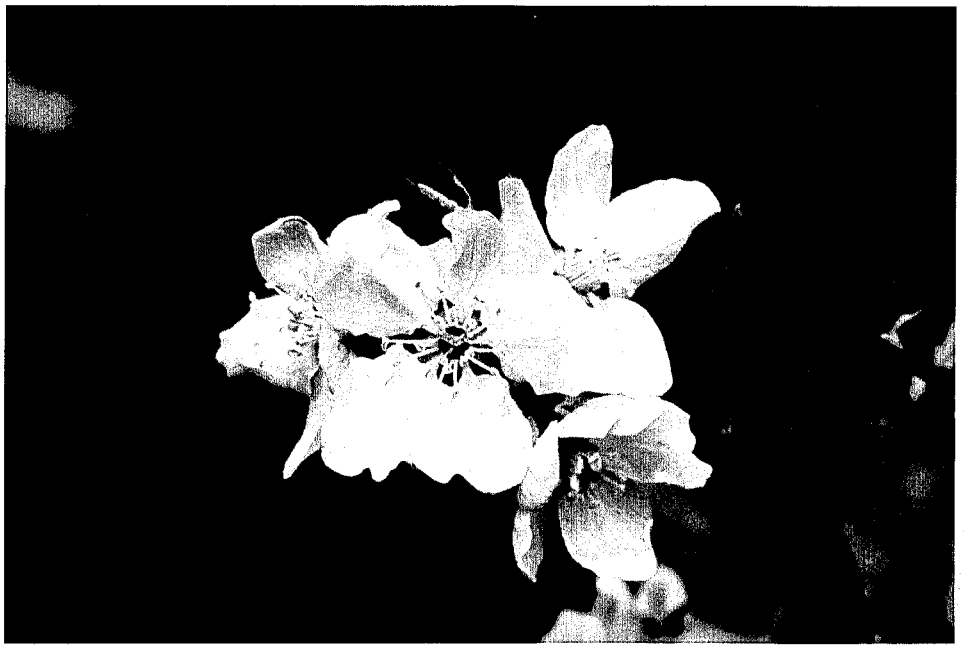
FIG. 9 is a photograph of a flower cluster of the new apple tree variety.
Figure 10:
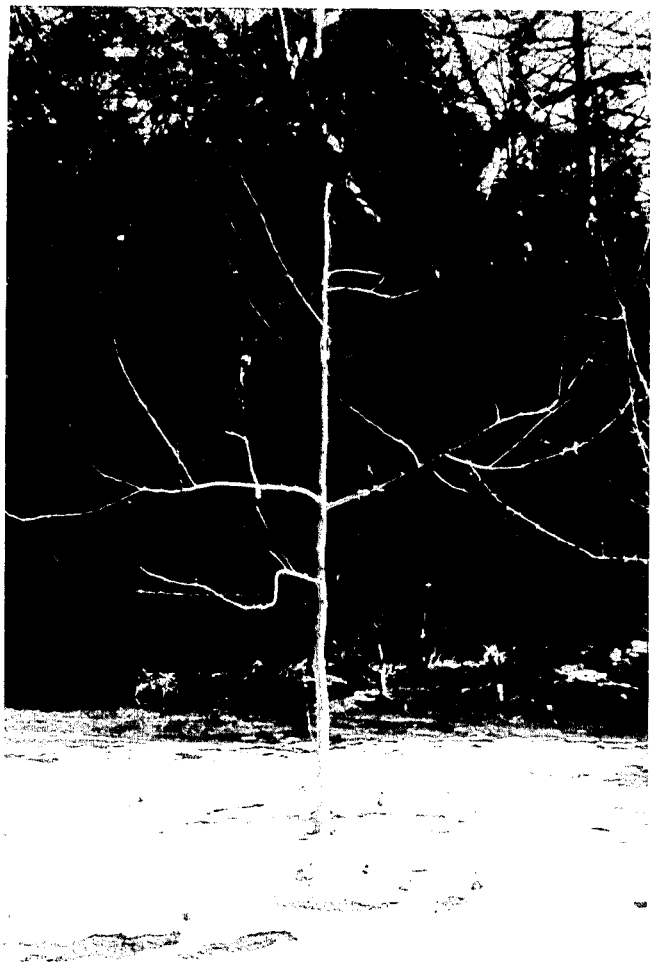
FIG. 10 is a photograph of the tree of the new apple tree variety in its entirety.
Figure 11:
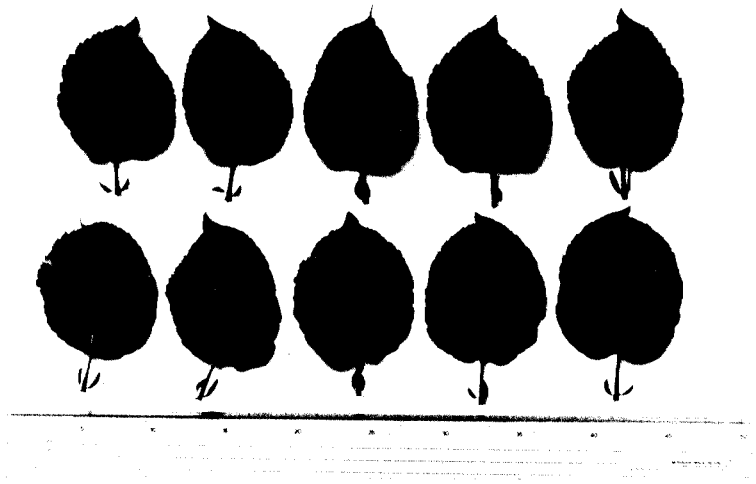
FIG. 11 is a photograph of the leaves of the new apple tree variety.
Figure 12:
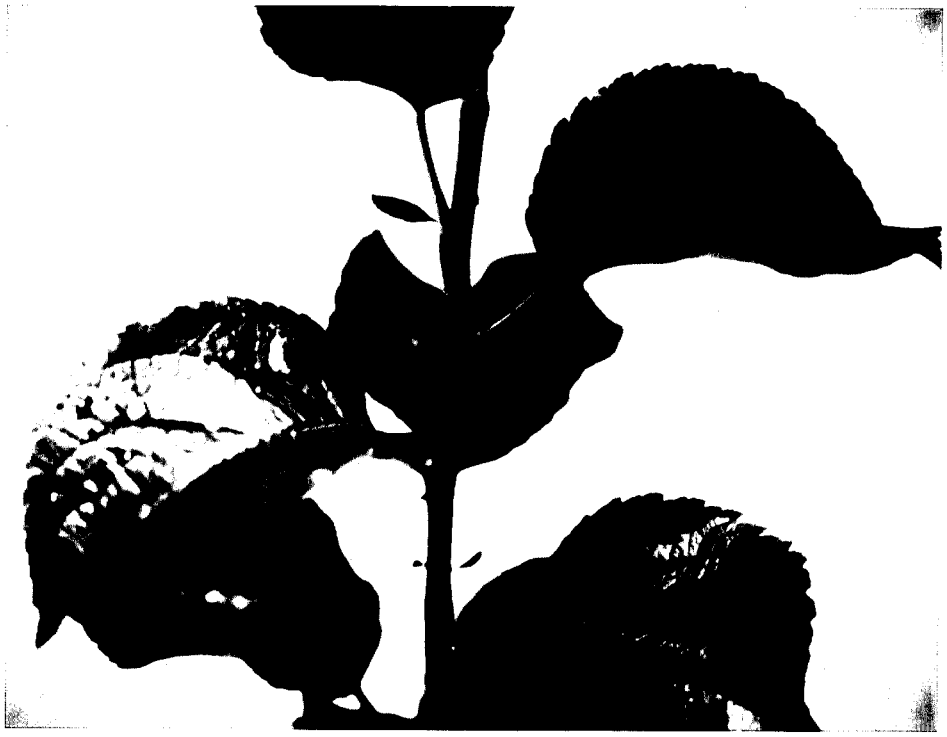
FIG. 12 is a photograph of a shoot of the new apple tree variety.

A detailed description of this new apple variety follows, with color terminology being given in accordance with the Munsell hue color chart, except where the color is obvious and described in color terms of ordinary dictionary significance.

A. Genus and species: *Malus pumila* Mill.

B. Name: Benifuji.

C. Type/Market Class: Fuji variety of apple tree.

The tree has been asexually reproduced by grafting and trees resulting from such asexual reproduction are true to the type of the original tree in all distinguishing characteristics.

D. Breeding history of the variety:

1. *Purpose of breeding.*—To produce an excellent dessert apple variety.
2. *Crossing.*—Fuji×Unknown.
3. *Process of breeding.*—Mr. Tsuneo Murakami, No. 2, Shinzo Nagane, Gonohe cho, Sannohe gun, Aomori Prefecture, crossed Fuji and an unknown in 1977. After 2 years, he selected one seedling distinguished by the features of a glossy leaf and late sprouting in 2000 seedlings, and grafted it on the seedling and Maruba rootstock. In 1986, the original tree and the tree based on the seedling bore their first crops. The fruit ripened early in the season and exhibited good eating and storage quality. The tree of this variety was transplanted for sparse planting and protection to other orchards of the breeders in April 1986.

E. Trials: In 1986, the original tree (10 years old) and the tree based on seedling (8 years old) bore 4 fruit and 50 fruit respectively. However, the tree based on Maruba never bore any fruit. In 1987, 40 fruit were picked on the tree based on the seedling.

F. General characteristics:

1. *Fruit.*—Round to oblong, 250 g (on seedling rootstock) slightly larger than known early maturing varieties. The color is a scarlet stripe on greenish yellow ground color. Dots on the fruit skin are much smaller than Tsugaru variety. Flesh is juicier and firmer than other early maturing varieties. The variety is sweeter (Brix 12.3, PH 3.7) than Kitanosachi variety and has a good eating quality.
2. *Harvest time.*—The variety is picked August 30 through September 2 (on seedling rootstock) at origin (Aomori Prefecture, Japan). This is 5 days before the Kitanosachi variety and 15–20 days before the Tsugaru variety.

3. *Storage.*—The fruit can be stored one month in cold storage at Aomori Prefecture, Japan. Vigor of the tree is weak, resembling Tsugaru variety.

4. *Blooming date.*—The typical blooming date is midseason. That is, at the same time as Fuji or one to two days earlier than Fuji.

G. Detailed characteristics:

1. *Tree.*—The tree formed as depicted is easily trained to a central leader habit with few, well-spaced scaffold branches having strong attachment to the main stem at angles approaching about 80°. The tree reaches an average height similar to that of Jonathan. Further, the fruiting is mainly on spurs and the tree does not prolifically branch. Habit of branches — spreading. Size — medium. Vigor — weak/medium. Dormant one year old shoot; diameter: 0.66 cm. Dormant one year old shoot; internode length — 2.51 cm. Dormant one year old shoot; size of lenticels — medium. Dormant one year old shoot; amount of lenticels — medium. Dormant one year old shoot; amount of pubescence — absent or very slight/weak. Dormant one year old shoot; Lateral fruit buds; numbers — medium. Dormant fruit buds; shape — conical or oval. Color 5 R $\frac{2}{3}$.

*Leaf.*—Configuration of surface — uncupped. Shape — round. Serration — serrate. Position of maximum breadth — at center. Length of leaf blade: 9.8 cm. Thickness of leaf blade: 8.0 cm. Apex — cuspidate. Base — cordate. Color — 5 GY $\frac{3}{4}$. Pubescence — medium. Surface — glossy. Stipule; shape — round conical. Stipule; size — medium. Substipule — absent. Petiole; length — 2.93 cm. Petiole; thickness — 0.20 cm.

3. *Flower.*—Numbers/cluster — medium. Size — medium. Unopened flower bud color — pale pink. Petal; shape — oval. Petal; numbers — medium. Stamen; numbers — medium. Anther; color — pale yellow. Pollen; amount — medium.

4. *Fruit.*—Symmetry — symmetric. Aperture of calyx — medium. Depth of calyx end — shallow. Breadth of calyx end — medium. Depth of stalk cavity — shallow. Breadth of stalk cavity — medium. Amount of russet of stalk cavity — absent. Thickness of stalk — medium. Length of stalk — medium. Ribs — indistinct. Size — medium. Ground color — yellowish green. Intensity of ground color — medium. Surface color — 5 R 4/11. Intensity of over color of skin — medium. Form of over color of skin — distinct stripe. Amount of over color of skin — medium. Russet of fruit; 1. Position — calyx end. 2. amount of russet — absent or very slight. Raised russet lenticls — absent. Size of lenticels — medium. Density of lenticels — medium. Scarf skin — absent. Shininess of skin — medium. Skin wax — medium. Skin cracking tendency — absent. Surface texture of skin — medium. Length of peduncle — medium. Thickness of peduncle — medium. Lipped — absent. Size of core — medium. Number of core cell — five. Color of the flesh — yellow. Bruising of the flesh — medium. Oxidation of flesh — medium. Firmness of the flesh — medium. Texture of the flesh — medium. Water core — absent. Sweetness of the flesh — medium. Acidity of the flesh — medium. Astringency of the flesh — absent. Flavor of the flesh — pleasant, no distinctive character. Juiciness of the flesh — medium. Seed; Number of seeds — 12.4 or average. Seed; Shape of seed — oblong. Seed; Size of seed — medium. Sprouting period — medium. Season of flowering — mid-season. Season of leaf fall — medium. Time of maturity for picking — early. Time of fruit ripening for eating — early (August). Precociousness in fruit setting — medium. Self-compatibility — medium. Physiological fruit drop: 1. Early drop — absent or very slight. 2. Preharvest drop — absent or very slight. Physiological disorder of fruit — medium. Storage life: 1. In natural storage — slightly long. 2. In cold storage — long. Resistance to: 1. Amount of moldy carpel — absent or slight. 2. Alternaria blotch — medium. 3. Powdery mildew — medium. 4. Rust — medium. 5. Scab — medium. Pest resistance: Aphis — medium.

H. Characteristics distinguishable from other varieties: The variety is distinguished from the Kitanosachi variety by having less fruit skin russet, but resembles Fuji, in coloring, good eating quality and early maturing time.

I. Breeding and propagation-purebred variety:

*Propagation.*—Hybrid variety. Vegetative propagation

J. Main use of the variety: Dessert and processing apple.

K. *Suggestion for growing: Pruning and training of the variety is relatively easy because of few spinal shoots. Productivity appears on many shoots. Cultivation is considered the same as for popular apple varieties.*

The pollination requirements and uniformity of productivity from year-to-year are similar to Jonathan.

I claim:

1. A new and distinct apple tree substantially as shown and described, particularly characterized by fruit which has less skin russet than Kitanosachi variety but a color, eating quality and maturing time resembling Fuji.

* * * * *

S. 62. 5. 12.